United States Patent
Babinski et al.

[11] Patent Number: 5,976,520
[45] Date of Patent: *Nov. 2, 1999

[54] FOAMABLE SKIN PREPARATIONS

[75] Inventors: Linda J. Babinski, Kenosha; James A. Limburg, Racine, both of Wis.

[73] Assignee: S. C. Johnson & Son, Inc., Racine, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/747,297

[22] Filed: Nov. 12, 1996

[51] Int. Cl.⁶ ....................................................... A61K 7/15
[52] U.S. Cl. .............................. 424/73; 424/401; 514/945
[58] Field of Search ....................... 424/401, 73; 514/945

[56] References Cited

U.S. PATENT DOCUMENTS

| | | | |
|---|---|---|---|
| 4,528,111 | 7/1985 | Su | 252/107 |
| 4,548,810 | 10/1985 | Zofchak | 424/59 |
| 4,744,979 | 5/1988 | Osipow | 424/73 |
| 4,917,823 | 4/1990 | Maile | 252/548 |
| 4,992,211 | 2/1991 | Casciani | 252/541 |
| 5,084,270 | 1/1992 | Ciaudelli | 424/59 |
| 5,340,571 | 8/1994 | Grace | 424/73 |
| 5,451,396 | 9/1995 | Villars | 424/73 |
| 5,500,211 | 3/1996 | George | 424/73 |
| 5,518,647 | 5/1996 | Zocchi | 252/174.17 |
| 5,534,265 | 7/1996 | Fowler et al. | 424/489 |

FOREIGN PATENT DOCUMENTS

| | | |
|---|---|---|
| 2639635 | 6/1990 | France . |
| 93/15711 | 8/1993 | WIPO . |
| 94/17783 | 8/1994 | WIPO . |
| 94/18292 | 8/1994 | WIPO . |

*Primary Examiner*—Gollamudi S. Kishore

[57] ABSTRACT

Disclosed herein are skin preparations that contain an amphoteric surfactant, a cellulosic ether and a fatty ester of polyethylene glycol. Also disclosed are methods for using these compositions for shaving and body wash purposes.

7 Claims, No Drawings

FOAMABLE SKIN PREPARATIONS

BACKGROUND OF THE INVENTION

The present invention relates to foamable skin preparations suitable for use as shaving preparations and body washes. More particularly it relates to formulations which contain a surfactant, a fatty ester of polyethylene glycol, and a cellulosic ether.

A wide variety of shaving creams, gels, and lotions are known. See e.g. U.S. Pat. No. 5,451,396. The disclosure of this patent and of all other publications referred to herein are incorporated by reference as if fully set forth herein. Also, a wide variety of personal cleansing compositions are known. See e.g. U.S. Pat. No. 5,534,265.

However, it is desirable for a single product to be useful as both a body cleanser and a shaving preparation, particularly for use by women who wish to shave their legs when showering. Standard soaps and body washes have good rinsability and are easy to apply over a wide area. However, a shaving preparation should preferably be designed for more localized application and provide blade protection.

Foamability is also important in that it permits tracking of where shaving has taken place, and also contributes to a consumer's perception that a product is likely to be protective. Standard body soaps often have poor foamability.

Fatty esters of polyethylene glycol are known to provide blade protection. They also contribute to good skin conditioning. However, they can inhibit foaming.

Thus, a need exists for an improved foamable skin preparation which can be used both for body wash and shaving preparation purposes

BRIEF SUMMARY OF THE INVENTION

In one aspect the invention provides a skin preparation which contains 0.5% to 50% by weight of an amphoteric surfactant, 0.01% to 2% by weight of a cellulosic ether, and 0.01% to 5% by weight of an ester of polyethylene glycol.

In a preferred form the ester is a $C_{12}$ to $C_{22}$ fatty ester (e.g. polyethylene glycol-8-distearate), the amphoteric surfactant is selected from the group consisting of betaine and sultaine, and the cellulosic ether is an alkyl hydroxyalkyl cellulose ether such as cetyl hydroxyethyl cellulose (sold under the trade name Natrosol® CS Plus from Aqualon Corporation). The formulation may also include preservatives, colorants, other surfactants, fragrances, vitamins, emollients, pigments, foam stabilizers, and humectants.

In another aspect the invention provides methods of shaving human skin. They involve applying the skin preparation of the present invention to the skin, rubbing the skin preparation until foam is formed, and then shaving the skin with a razor.

The most preferred amphoteric surfactants are betaines and sultaines, such as lauramidopropyl betaine. However, a wide variety of other amphoteric (and other surfactants) can also be included, such as sodium lauroyl sarcosinate.

Further examples of amphoteric surfactants which can be used are derivatives of aliphatic secondary and tertiary amines in which the aliphatic radical can be straight or branched chain and wherein one of the aliphatic substituents contains from about 8 to about 22 carbon atoms (preferably $C_8$–$C_{18}$). Examples are alkyl imino acetates, and iminodialkanoates and aminoalkanoates of the formulas $RN[(CH_2)_m CO_2M]_2$ and $RNH(CH_2)_mCO_2M$ wherein m is from 1 to 4, R is a $C_8$–$C_{22}$ alkyl or alkenyl, and M is H, alkali metal, alkaline earth metal, ammonium, or alkanolammonium. Also included are imidazolinium and ammonium derivates.

Specific examples of other suitable amphoteric surfactants include sodium 3-dodecyl-aminopropionate, sodium 3-dodecylaminopropane sulfonate, N-alkyltaurines, N-higher alkyl aspartic acids, and the products sold under the trade name "Miranol". Other examples of useful amphoterics include phosphates, such as cocamidopropyl PG-dimonium chloride phosphate (commercial available as Monaquat PTC, from Mona Corp.).

Other examples of suitable betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxyethyl) carboxymethyl betaine, oleyl dimethyl gamma-carboxypropyl betaine, lauryl bis-(2-hydroxypropyl) alphacarboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Suitable sultaines (including the hydroxysultaines) include cocamidopropyl hydroxysultaine (available as Mirataine CBS from Rhone-Poulenc), and alkylsultaines, alkylamidopropyl hydroxy sultaines, and alkyl hydroxy sultaines. Examples are cocosultaine, lauryl sultaine, cocohydroxy sultaine, erucamidopyropylhydroxy sultaine, laurylhydroxy sultaine, oleamidopropylhydroxy sultaine, and tallowamidopropylhydroxy sultaine.

Also useful are the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g. triethanolamine), a preferred example of which is sodium lauroyl sarcosinate.

Other surfactants that can be included are sodium cetearyl sulfate, sodium lauryl sulfate, sodium lauryl sarcosinate, sodium cocoyl isethionate, coamidopropyl betaine, sodium laureth sulfate, ammonium laureth sulfate, lauramphodiacetate, cetyl dimethyl betaine, ammonium lauryl sulfate, sodium tallow soap, sodium coconut soap, ceteth-10, steareth-21, steareth-2, ceteth-2, glyceryl stearate, glucose amides, dilauryl dimethyl ammonium chloride, disteryl dimethyl ammonium chloride, dimyristyl dimethyl ammonium chloride, dipalmityl dimethyl ammonium chloride, and mixtures thereof.

A wide variety of hydroxyalkyl cellulose ethers (preferably alkyl hydroxyalkyl cellulose ethers) should also be suitable. These include, without limitation, carboxymethyl hydroxyethyl cellulose, hydroxyethyl cellulose, hydroxyethyl ethyl cellulose, hydroxypropyl cellulose, hydroxypropyl methyl cellulose, and methyl hydroxyethyl cellulose. Most preferred among alkyl hydroxyalkyl cellulose ethers is a material given the CTFA designation cetyl hydroxyethyl cellulose which is the ether of cetyl alcohol and hydroxyethyl cellulose. The material is sold under the trade name Natrosol® CS Plus.

The preferred $C_{12}$–$C_{22}$ fatty ester of polyethylene glycol is polyethylene glycol 8 distearate "PEG-8 distearate". Other potential polyethylene glycol ethers are PEG-2 stearate, PEG-4 stearate, PEG-6 stearate, PEG-8 stearate, PEG-10 stearate, PEG-12 stearate, and PEG-n distearate, where n=2 to 175, and other PEG-n-stearates where n=2 to 150.

Notwithstanding the normal tendency of fatty esters of polyethylene glycol to suppress foamability of surfactants, in the formulations of the present invention the preparations have very good flash foamability while retaining good blade protection and skin feel. Further, amphoterics are efficient cleaners with good rinsability. The viscosity control provided by the cellulosic ethers helps the shaving foam stay in place in a shower environment.

The objects of the present invention therefore include providing a foamable skin preparation which:

(a) is useful as a shaving preparation;

(b) is useful as a body wash;

(c) is easy to apply, spread and rinse; and (d) has desirable cleaning, tracking, moisturizing and blade protection properties.

These and still other objects and advantages of the present invention (e.g. methods for using such preparations) will be apparent from the description which follows. The following description is merely of the preferred embodiments. Thus, the claims should be looked to in order to understand the full scope of the invention.

DETAILED DESCRIPTION

EXAMPLE 1

The preferred skin preparation of the present invention contains the following ingredients:

| Ingredient | Weight Percentage | Function |
|---|---|---|
| sodium cocoyl isethionate (50% strength) | 7.5% water 7.5% active (Total 15%) | surfactant |
| lauroamidopropyl betaine | 20% | surfactant |
| Glycerine, USP (99.5% strength) | 3% | humectant |
| sodium lauroyl sarcosinate (30% strength) | 3.5% water 1.5% active (Total 5%) | surfactant |
| fragrance | .5% | fragrance |
| lauramido propyl amine oxide | 2% | foam stabilizer |
| polymeric quaternium ammonium salt of acrylamide and dimethyl diallyl ammonium chloride monomers - "Polyquaternium 7" | .5% | conditioner |
| polyethylene glycol-8 distearate | .5% | blade protection; skin feel adjuster |
| Stabileze 06 - (PVM/MA decadiene crosspolymer) | .21% | foam stabilizer |
| triethanolamine (99%) | .21% | pH adjuster |
| sorbitol (70%), USP | .3% water .7% active (Total 1%) | humectant |
| colorants | .0011% | colorant |
| Natrosol ® CS Plus | .2% | viscosity control agent |
| vitamin E acetate, USP | .1% | moisturizer |
| Kathon CG (Rohm & Haas) | .0015% | preservative |
| deionized water | to 100% | solvent |

This is made by the following mixing process. We added ¾ of the water to the glycerine, sorbitol, and colorants. We then added the Stabilese 06 and heated to 185° F. and mixed for one hour. We added PEG distearate and mixed well, and then the triethanolamine. Next we added sodium cocoyl isethionate at around 150° F., then the sarcosinate and amine oxide. We next added Polyquaternium 7, the betaine, and the remaining water and then cooled to 100° F. Finally, we added the vitamin, fragrance and preservative.

EXAMPLE 2

The following composition was prepared.

| Ingredient | Weight Percentage | Function |
|---|---|---|
| sodium cocoyl isethionate (50% strength) | 7.5% water 7.5% active (Total 15%) | surfactant |
| cocoamidopropyl betaine | 15% | surfactant |
| Glycerine, USP (99.5% strength) | 3% | humectant |
| sodium lauroyl sarcosinate (30% strength) | 3.5% water 1.5% active (Total 5%) | surfactant |
| cocoamido propyl amine oxide | 2% | foam stabilizer |
| polyethylene glycol-8 distearate | .5% | blade protection; skin feel adjuster |
| sorbitol (70%), USP | .3% water .7% active (Total 1%) | humectant |
| Natrosol ® 250 HHR (hydroxy ethyl cellulose) | .2% | viscosity control agent |
| vitamin E acetate, USP | .1% | moisturizer |
| Kathon CG (Rohm & Haas) | .0015% | preservative |
| deionized water | to 100% | solvent |

The above above formulation was prepared in a manner similar to EXAMPLE 1:

EXAMPLE 3

The following composition was prepared.

| Ingredient | Weight Percentage | Function |
|---|---|---|
| sodium cocoyl isethionate (50% strength) | 5% water 5% active (Total 10%) | surfactant |
| lauroamidopropyl betaine | 20% | surfactant |
| Glycerine, USP (99.5% strength) | 3% | humectant |
| sodium lauroyl sarcosinate (30% strength) | 3.5% water 1.5% active (Total 5%) | surfactant |
| lauramphodiacetate | 10% | foam stabilizer |
| polyethylene glycol | 1.0% | conditioner |
| polyethylene glycol-150 distearate | .2% | blade protection; skin feel adjuster |
| triethanolamine (99%) | .02% | pH adjuster |
| sorbitol (70%), USP | .3% water .7% active (Total 1%) | humectant |
| Methocel 40–100 (Hydroxy propyl methyl cellulose) | .2% | viscosity control agent |
| vitamin E acetate, USP | .1% | moisturizer |
| deionized water | to 100% | solvent |

The above formulation was prepared in a manner similar to EXAMPLE 1:

EXAMPLE 4

The following composition was prepared.

| Ingredient | Weight Percentage | Function |
|---|---|---|
| sodium cocoyl isethionate (50% strength) | 5% water 5% active (Total 10%) | surfactant |
| lauroamidopropyl betaine | 20% | surfactant |
| Glycerine, UPS (99.5% strength) | 3% | humectant |
| ammonium laureth sulfate 2EO | 10% | surfactant |
| propylene glycol | 1.0% | conditioner |
| polyethylene glycol-150 distearate | .5% | blade protection; skin feel adjuster |
| Citric acid | .1% | pH adjuster |
| sorbitol (70%), USP | .3% water .7% active (Total 1%) | humectant |
| colorants | .0011% | colorant |
| Natrosol ® 250 HHR | .5% | viscosity control agent |
| vitamin E acetate, USP | .1% | moisturizer |
| Kathon CG (Rohm & Haas) | .0015% | preservative |
| sodium chloride | .5 | viscosity control agent |
| deionized water | to 100% | solvent |

The above formulation was prepared in a manner similar to EXAMPLE 1.

We have also successfully tested various other formulations within the following ranges: 10–30% ammonium lauryl ether sulfate (30% active); 5–25% sodium cocoyl isethionate (48% active); 5–20% betaine/sultaine (30–35% active); 1–10% humectant; 0.1–5% PEG-distearate; and 0.01–2% cetyl hydroxyethyl cellulose.

Our formulations were tested on human beings. One set of tests evaluated lathering: Formulations were blind-label tested by laboratory personnel using a hand washing technique to evaluate lathering characteristics. They washed their hands before beginning the evaluation. They applied approximately 1 teaspoon of product to the palm of their wet hands. They rubbed their hands together to generate lather, noting the speed of foaming, amount of lather, and foam texture. A composite score from 0 to 5 was given for each formulation and for comparison products. The scores were then averaged and written comments were noted. The testers reported that the formulations provided good foamability.

Another set of tests related to shaving. Shaving performance was determined by a women's shave panel. The participants used the product and favorably evaluated the performance by answering a performance questionnaire.

INDUSTRIAL APPLICABILITY

The present invention provides compositions useful as a body wash and shaving preparation.

We claim:

1. A skin preparation that is a shaving preparation, comprising:

0.5% to 50% by weight of amphoteric surfactant selected from the group consisting of betaines and sultaines;

0.01% to 2% by weight of cellulosic ether;

0.01% to 5% by weight of $C_{12}$–$C_{22}$ ester of polyethylene glycol; and at least 10% by weight of water;

wherein the preparation is a preparation that can foam when rubbed on human skin.

2. The skin preparation of claim 1, wherein the cellulosic ether is a hydroxyalkyl cellulose ether.

3. The skin preparation of claim 2, wherein the cellulosic ether is an alkyl hydroxyalkyl cellulose ether.

4. The skin preparation of claim 1, wherein the preparation further comprises an amine oxide.

5. The skin preparation of claim 1, wherein the ester of polyethylene glycol is a $C_{12}$–$C_{22}$ fatty ester of polyethylene glycol.

6. The skin preparation of claim 1, wherein the skin preparation is also a liquid cleanser.

7. A method of shaving a human skin surface having hair projecting therefrom, comprising:

applying the shaving preparation of claim 1 to the surface;

rubbing the preparation on the skin surface until a foam is formed on the surface; and then shaving the surface with a razor.

* * * * *